United States Patent
Kadobayashi et al.

(10) Patent No.: US 7,918,665 B2
(45) Date of Patent: Apr. 5, 2011

(54) ARTIFICIAL ANTERIOR TOOTH HAVING FRICTIONAL SURFACE AT LINGUAL SIDE, AND A SET OF ARTIFICIAL TEETH, AND DENTURE

(75) Inventors: Yusei Kadobayashi, Kyoto (JP); Toshihide Fujii, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 12/634,993

(22) Filed: Dec. 10, 2009

(65) Prior Publication Data
US 2010/0151422 A1 Jun. 17, 2010

(30) Foreign Application Priority Data

Dec. 16, 2008 (JP) ................... 2008-319122
Oct. 8, 2009 (JP) ................... 2009-234295

(51) Int. Cl.
*A61C 13/08* (2006.01)
(52) U.S. Cl. ................... 433/197; 433/202.1
(58) Field of Classification Search ........... 433/18–19, 433/167–172, 191, 197, 202.1, 209, 215, 433/218–223
See application file for complete search history.

(56) References Cited

U.S. PATENT DOCUMENTS

| 647,400 | A | * | 4/1900 | Glew | 433/197 |
| 2,144,198 | A | * | 1/1939 | Page | 433/197 |
| RE24,045 | E | * | 7/1955 | Dahl et al. | 433/191 |
| 2,768,440 | A | * | 10/1956 | Elliott | 433/191 |
| 3,252,220 | A | * | 5/1966 | Goddard | 433/197 |
| 6,464,495 | B1 | | 10/2002 | Voudouris | |

FOREIGN PATENT DOCUMENTS

JP 7-67890 3/1995

OTHER PUBLICATIONS

Sato et al, Machine Translation of JP 07-067890, Mar. 1995, accessed at JPO website on Apr. 20, 2010.*
Notice of Reason for Rejection (in English language) issued Feb. 9, 2010 in corresponding Japanese Patent Application No. 2009-234295.

* cited by examiner

*Primary Examiner* — Cris L Rodriguez
*Assistant Examiner* — Edward Moran
(74) *Attorney, Agent, or Firm* — Wenderoth, Lind & Ponack, L.L.P.

(57) ABSTRACT

An artificial anterior tooth capable of grinding food is provided. The lingual side of an artificial anterior tooth is provided with a protuberance for forming a frictional surface dented in an arch shape as seen from the mesiodistal direction, and the labial side of an opposite artificial lower tooth is provided with a protuberance for forming a sliding surface abutting the frictional surface and sliding on the frictional surface by a sliding motion of the upper and lower jaws.

8 Claims, 6 Drawing Sheets

ARTIFICIAL ANTERIOR TOOTH HAVING FRICTIONAL SURFACE AT LINGUAL SIDE, AND A SET OF ARTIFICIAL TEETH, AND DENTURE

BACKGROUND OF THE INVENTION

1. Field of the Invention

The present invention relates to an artificial anterior tooth, a set of artificial teeth, and a denture.

2. Description of the Related Art

In natural teeth, anterior teeth have the function of biting off the food, and molar teeth have a function of crushing and grinding the food. When the anterior teeth are occluded in intercuspal position (the molar teeth being in clenching status), the maxillary teeth are positioned to the labial side by 2 to 3 mm from the mandibular teeth, so that both teeth do not conflict with each other. When biting off the food by the anterior teeth, the lower jaw is shifted forward to bite so that the cutting edge of the maxillary anterior teeth and the cutting edge of the mandibular anterior teeth may abut on each other.

Conventionally, the artificial teeth are manufactured with the purpose of reproducing the functions of the natural teeth, but when arranged on the denture, it is hard to obtain a sufficient masticatory function that is the same as in natural teeth. It has been therefore attempted to provide the artificial teeth with a masticatory function not available in the natural teeth, so that the comprehensive masticatory capacity may be equivalent to that of the natural teeth as closely as possible.

For example, JP-A-07-67890 discloses an invention in which a platform of a horizontal plane is formed about 3 mm above the cutting edge at the lingual side of the maxillary incisors, and with the molar teeth being occluded in the intercuspal position, the cutting edge of the mandibular incisors are abutted on this platform, so that the function of biting off food is added. According to this invention, when biting and grinding food by occluding the molar teeth, the food can be cut off by the anterior teeth. However, when grinding food by the molar teeth, it is preferred to provide the anterior teeth with the grinding function, rather than the biting function.

SUMMARY OF THE INVENTION

In the light of the problems discussed above, it is an object of the present invention to provide an artificial anterior tooth and a set of artificial teeth capable of grinding food, and a denture using such artificial anterior teeth.

To achieve the above object, the present invention provides an artificial anterior tooth having a protuberance forming a frictional surface capable of friction contacting with an opposite tooth, at a lingual side.

With this configuration, the food can be ground by bringing the opposite tooth into friction contact with the frictional surface formed in the artificial anterior tooth.

In the artificial tooth of the invention, the protuberance is preferably provided with a groove extending from the cutting edge in a direction toward the cervical portion so as to move the food once ground on the frictional surface aside to the outside of the frictional surface, so as to be ground further.

In the artificial tooth of the present invention, the frictional surface is preferably dented in an arch form as seen from the mesiodistal direction so that the food can be ground by the natural occlusal motion, and more preferably a shape profiling the sliding motion of the molar tooth should be included so that the food can be ground by the siding motion of the molar tooth.

Because the maxillary anterior teeth are positioned at the labial side of the mandibular anterior teeth in ordinary occlusion, the artificial tooth of the present invention is preferred to be a maxillary anterior tooth.

The set of artificial teeth of the present invention has plural artificial teeth including any one of the artificial anterior teeth, and preferably the artificial anterior tooth opposite to the artificial anterior tooth having the frictional surface should be provided with a protuberance, at the labial side, for forming a sliding surface having a function of a cusp for grinding the food by friction contact with the frictional surface. The sliding surface formed by this protuberance abuts the frictional surface, so that the cutting edge may not be worn out due to contact with the frictional surface.

In the set of artificial teeth of the present invention, as in the dentition of natural teeth, plural artificial anterior teeth may be opposite to the artificial anterior tooth having the frictional surface, and in this case the protuberance forming the sliding surface may be provided in each one of the opposite artificial anterior teeth.

The denture of the present invention includes any one of the set of artificial teeth arranged on the denture base, and in order to grind the food by the frictional surface by the food grinding motion of the molar teeth, the frictional surface should preferably abut on the labial side of the opposite artificial teeth at the intercuspal position.

According to the present invention, since the lingual side of the artificial anterior tooth is provided with the frictional surface to friction contact with the labial side of the opposite tooth, food can be ground by the anterior tooth when biting the molar teeth.

BRIEF DESCRIPTION OF THE DRAWINGS

An embodiment of the present invention is described below with reference to the accompanying drawings, in which.

DETAILED DESCRIPTION OF THE INVENTION

Figure 1:
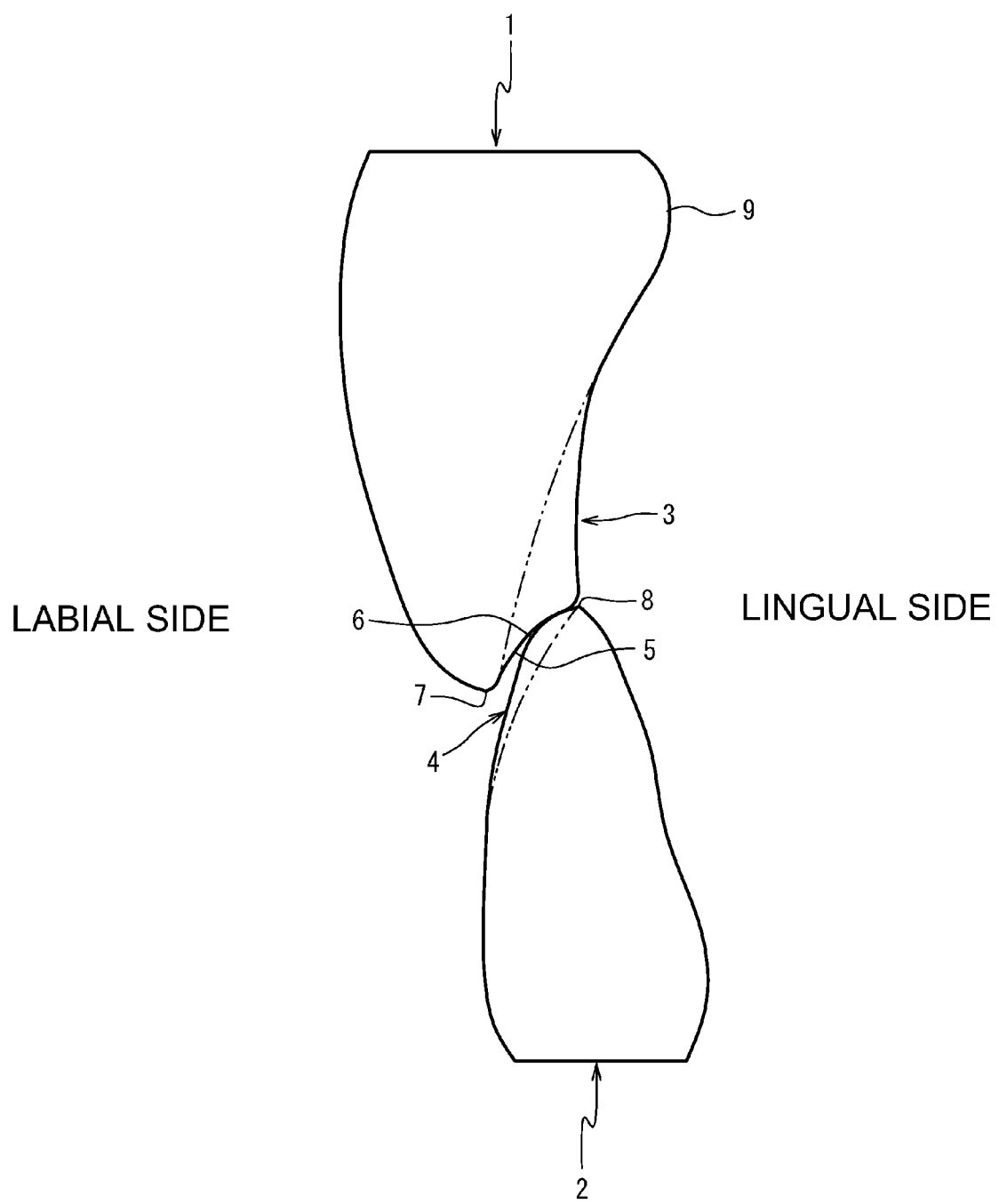
FIG. 1 is a side view of mutually opposite artificial upper central incisor and artificial lower central incisor in an embodiment of the present invention.
Figure 2:
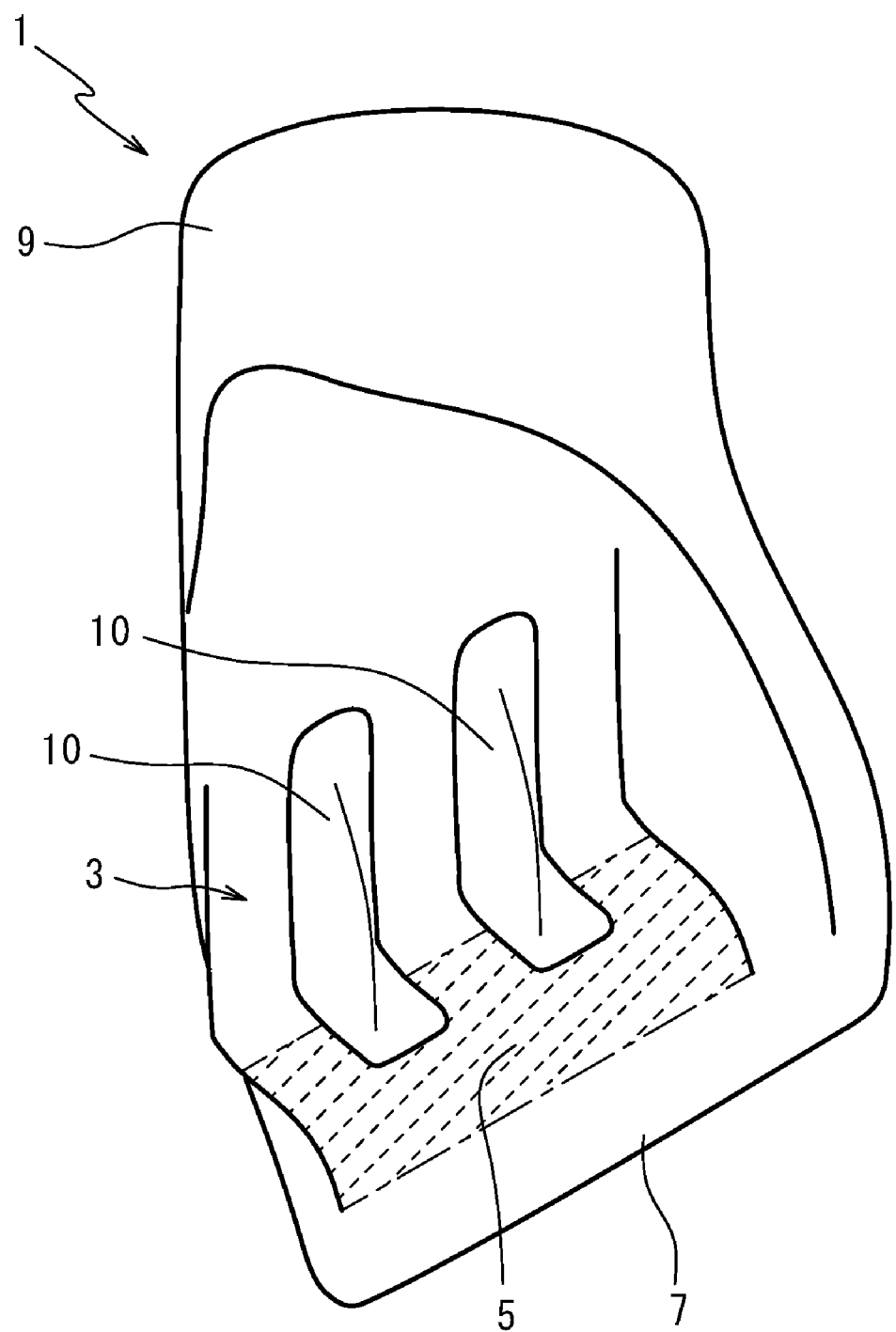
FIG. 2 is a perspective view of the artificial upper central incisor of FIG. 1.
Figure 3:
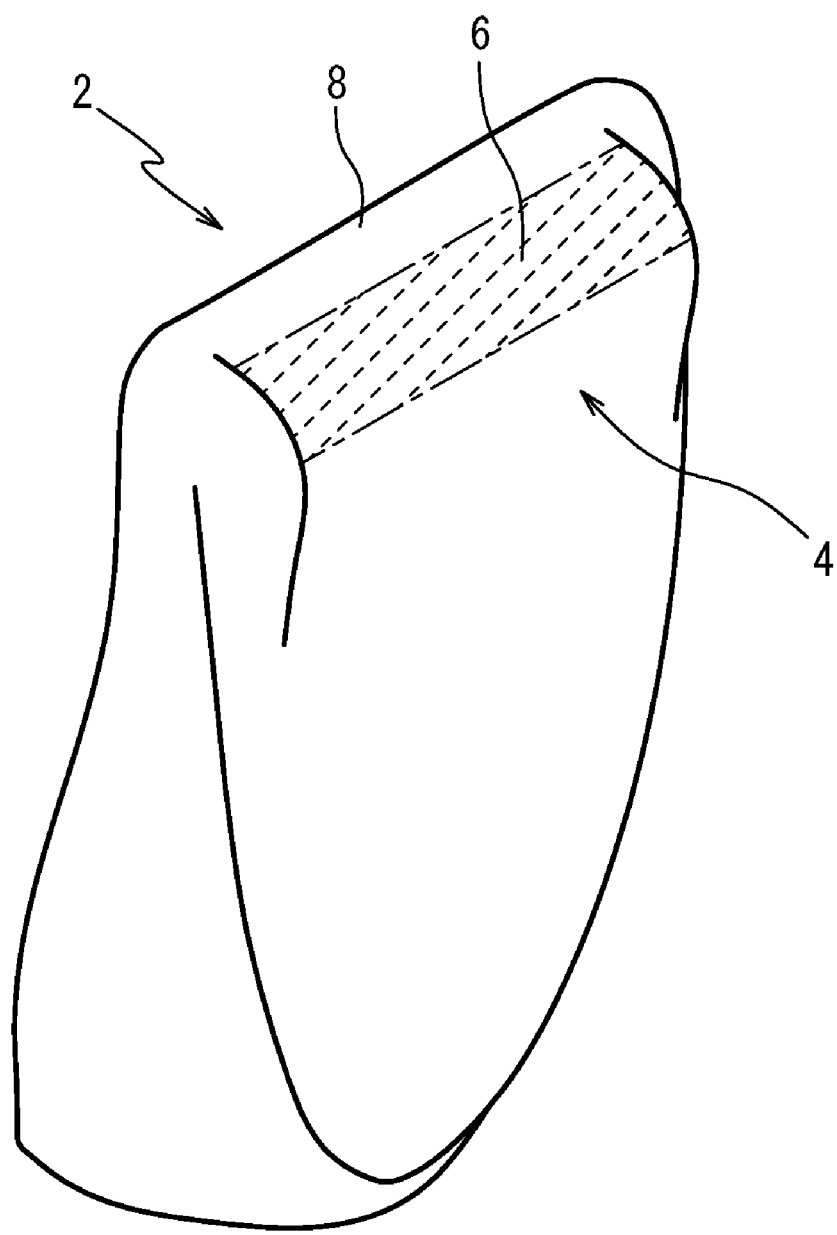
FIG. 3 is a perspective view of the artificial lower central incisor of FIG. 1.

FIG. 1 is a mesial side view (the straight lateral side as seen from the median) of mutually opposite artificial upper central incisor 1 and artificial lower central incisor 2 in an embodiment of the present invention, FIG. 2 shows a lingual side shape of the artificial upper central incisor 1, and FIG. 3 shows a labial side shape of the artificial lower central incisor 2.

The artificial upper central incisor 1 has a protuberance 3, at the lingual side, projecting prominently as compared with the shape of the natural tooth indicated by double dot chain line in FIG. 1. The artificial lower central incisor 2 has a protuberance 4, at the labial side, projecting prominently from the natural tooth. In FIG. 2 and FIG. 3, in order to emphasize the shape of the protuberances 3, 4, the edge is clearly shown, but actually the protuberances 3, 4 are preferred to be formed of smooth curves without edges.

The protuberance 3 of the artificial upper central incisor 1 and the protuberance 4 of the artificial lower central incisor 2 respectively form frictional surface 5 and sliding surface 6 that are in friction contact with each other, by the occlusal motion of the upper jaw and the lower jaw. As shown in FIG. 1, the frictional surface 5 of the artificial upper central incisor 1 is dented in an arch form as seen from the mesiodistal direction, and the sliding surface 6 of the artificial lower central incisor 2 is bulged in an arch form as seen from mesiodistal direction. The frictional surface 5 and the sliding surface 6 are formed respectively away from cutting edges 7, 8 of the artificial central incisors 1, 2.

Further, the protuberance 3 of the artificial upper central incisor 1 is extended from the cutting edge 7 toward a cervical portion 9, and has two grooves 10 opened to the sliding surface 5 at the cutting edge 7 side. At the lingual side of the natural central incisor, two shallow recesses extended from the cutting edge toward the cervical portion are present, and therefore in the present embodiment, by modeling after this configuration, two grooves 10 are formed in the protuberance 3, but the number of grooves 10 may be one or three or more. The width of the groove 10 in the mesial extending direction is preferably 1 to 2 mm, and more preferably 1.2 to 1.5 mm. Preferably, the grooves 10 should be formed so that plural convex portions extended from the cutting edge 7 toward the cervical portion 9 formed by the grooves 10 of the protuberance 3 may be nearly equal in pitch and equal width, and may be distributed uniformly at the lingual side of the artificial upper central incisor 3.

Figure 4:
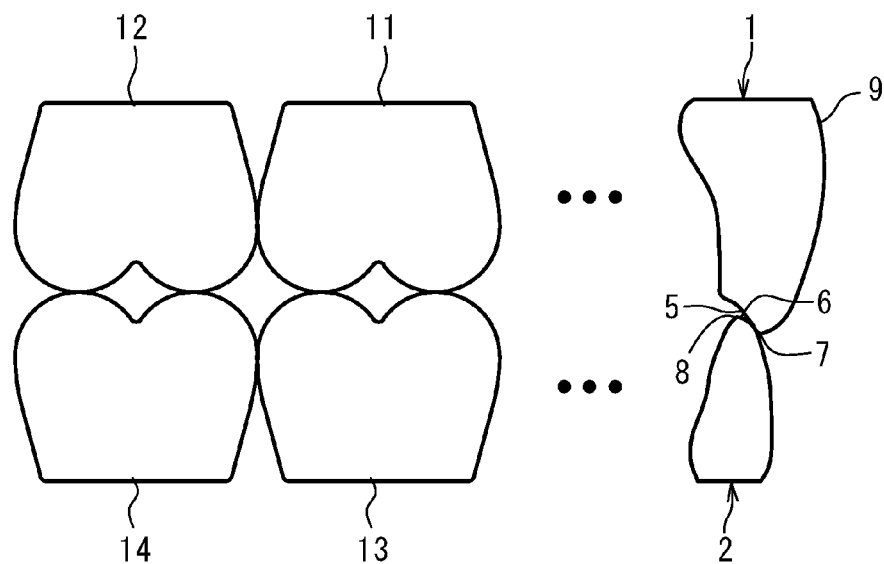
FIG. 4 is a view showing a positional relation in a mutually abutting state of cusps of upper and lower molar teeth in the artificial central incisors of FIG. 1.
Figure 5:
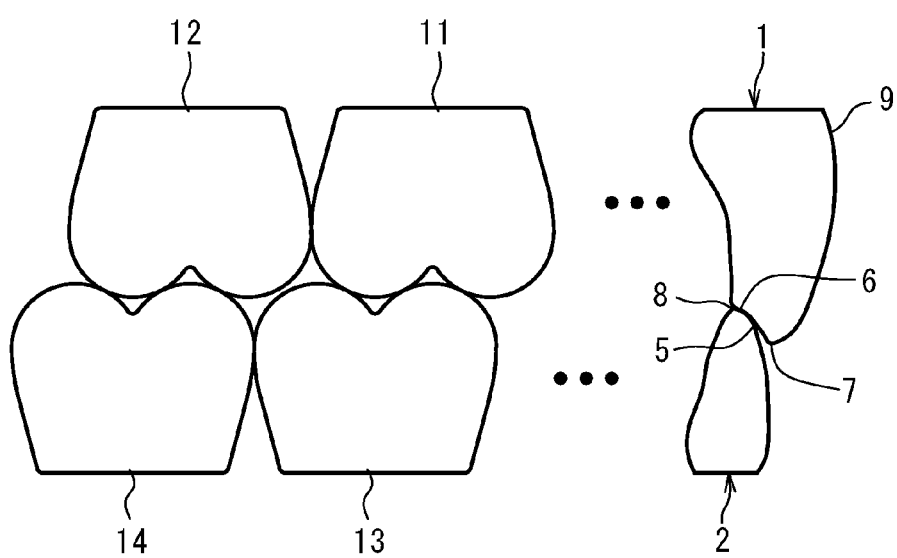
FIG. 5 is a view showing a positional relation in occluded position at intercuspal position in the artificial central incisors of FIG. 1.

FIG. 4 and FIG. 5 show the positional relation of the artificial central incisors 1, 2, together with the positional relation of upper molar teeth 11, 12 and lower molar teeth 13, 14. The relative positions of the artificial upper central incisor 1 and upper molar teeth 11, 12, and the artificial lower central incisor 2 and lower molar teeth 13, 14 are determined when the artificial central incisors 1, 2 are fixed on denture bases.

As shown in FIG. 4, at the abutting position between the cusp of the upper molar teeth 11, 12 and the cusp of the lower molar teeth 13, 14, the sliding surface 6 of the artificial lower central incisor 2 abuts on the end portion of the cutting edge 7 side of the frictional surface 5 of the artificial upper central incisor 1. Further, by sliding the upper molar teeth 11, 12 and lower molar teeth 13, 14, as shown in FIG. 5, when the upper jaw and the lower jaw are occluded at the intercuspal position (central occlusal position), the sliding surface 6 of the artificial lower central incisor 2 abuts on the end portion of the cervical portion 9 side of the frictional surface 5 of the artificial upper central incisor 1. In other words, the sliding surface 6 is formed in a shape profiling to the trace of the sliding motion of the molar teeth 11, 12, 13, 14, and by this sliding motion of the upper and lower jaws, the sliding surface 6 slides on the frictional surface 5.

In order that the sliding surface 6 may slide smoothly on the frictional surface 5, it is important to keep the contact surface between the frictional surface 5 and the sliding surface 6 not so large. Accordingly, in this embodiment, the curvature of the sliding surface 6 is smaller than the curvature of the frictional surface 5.

By sliding motion between the frictional surface 5 of the artificial upper central incisor 1 and the sliding surface 6 of the artificial lower central incisor 2, the food held between the frictional surface 5 and the sliding surface 6 can be ground. Furthermore, the food ground between the frictional surface 5 and the sliding surface 6 is forced out into the grooves 10 of the artificial upper central incisor 1, and therefore escapes from the sliding surface 5 in the direction of the cervical portion 9, so that the food remaining between the frictional surface 5 and the sliding surface 6 can be further ground finely.

At the intercuspal position, the sliding surface 6 of the artificial lower central incisor 2 abuts on the end portion of the opened side of the grooves 10 of the frictional surface 5 of the artificial upper central incisor 1. As a result, the bottom of the grooves 10 is opened at the labial side of the artificial lower central incisor 2, and an air passage communicating between the oral cavity and the labial side is formed, so that the user of the denture may not feel suffocation.

Figure 6:
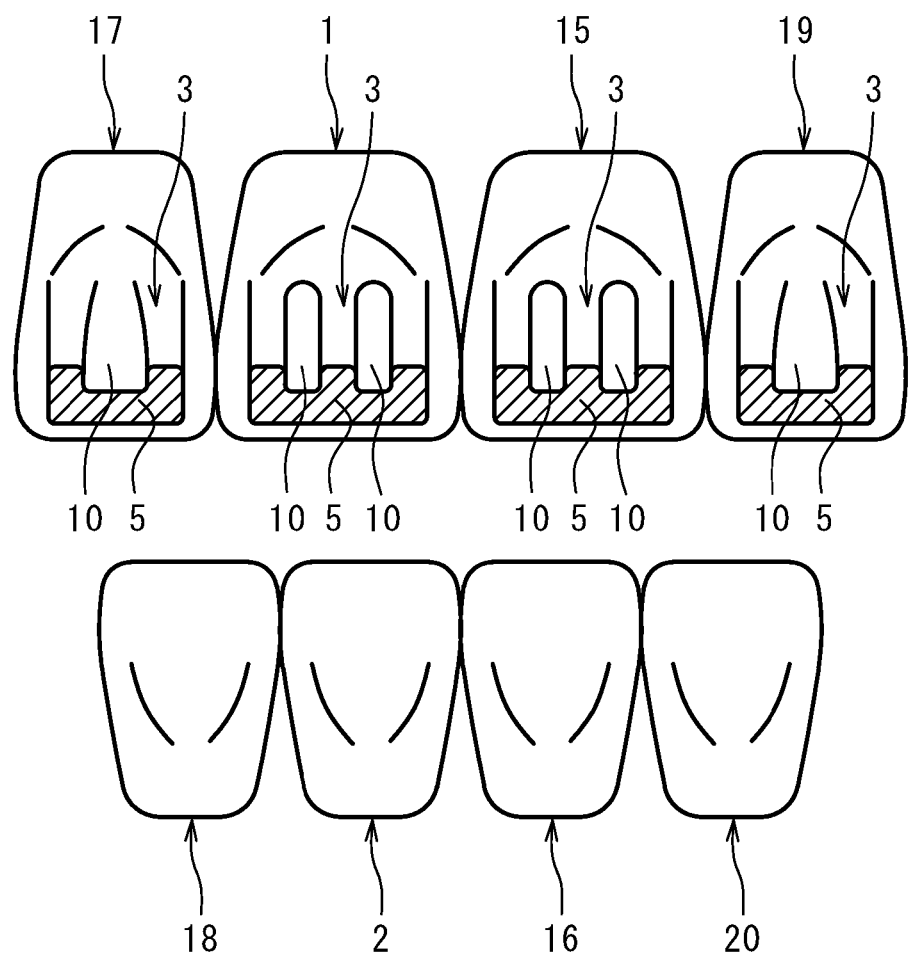
FIG. 6 is a view of lingual side of the set of artificial teeth including the artificial central incisors of FIG. 1.
Figure 7:
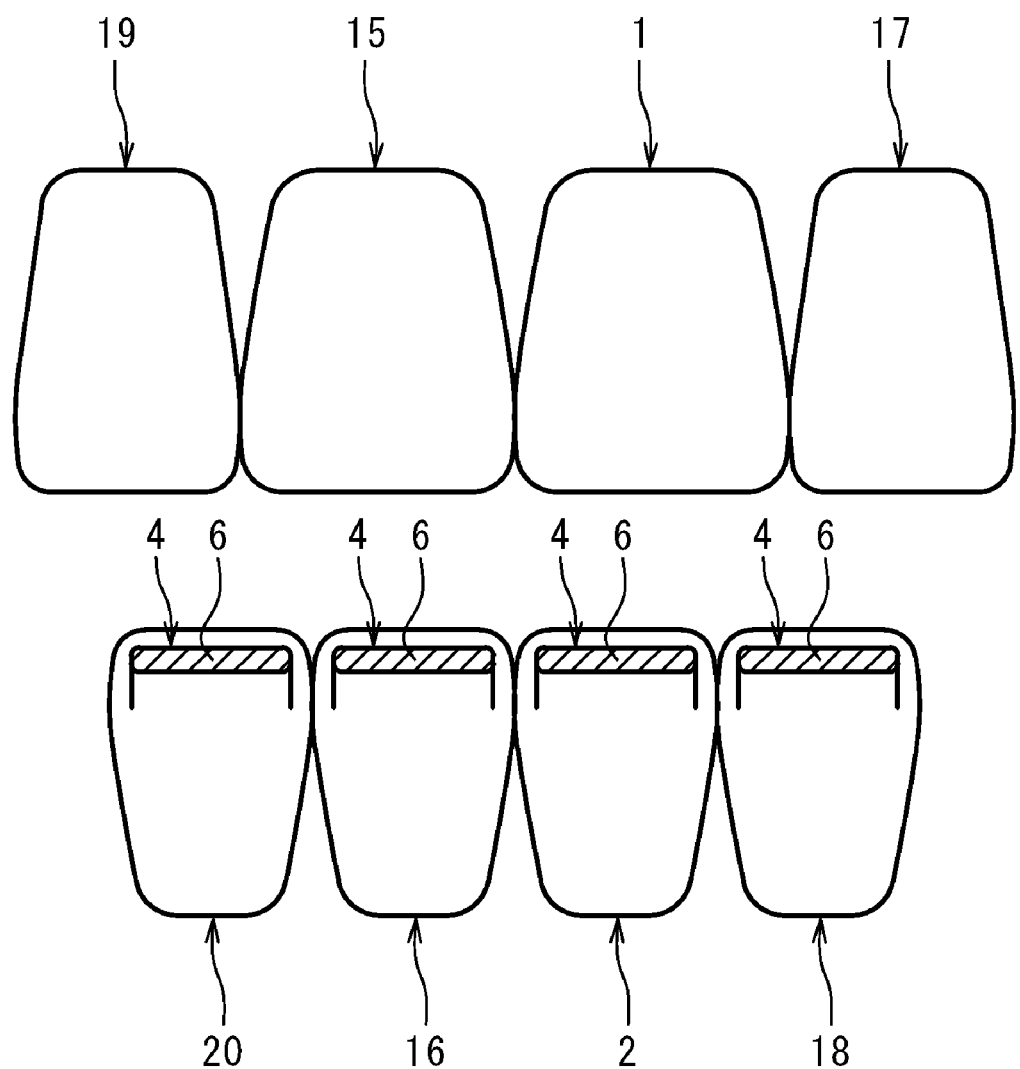
FIG. 7 is a view of labial side of the set of artificial teeth of FIG. 6.

FIG. 6 and FIG. 7 show the lingual side and the labial side of the set of artificial teeth including the artificial central incisors 1, 2. As show in the figure, this set of artificial teeth is a set of artificial incisors including artificial central incisors 15, 16, artificial upper lateral incisors 17, 19, and artificial lower lateral incisors 18, 20 formed as a right and left pair corresponding to the artificial central incisors 1, 2.

The artificial upper incisors 15, 17, 19 are respectively provided with protuberances 3 forming frictional surfaces 5, which are the same as in the artificial upper central incisor 1, and the artificial lower incisors 16, 18, 20 are respectively provided with protuberances 4 forming sliding surfaces 6, which are the same as in the artificial lower central incisor 2.

The artificial upper central incisors 1, 15 are opposite not only to the artificial lower central incisors 2, 16, but also partly to the artificial lower lateral incisors 18, 20, and the sliding surface 6 of the artificial lower lateral incisors 18, 20 abuts also on the frictional surface 5 of the artificial upper central incisors 1, 15.

As the width of upper central incisors is about 6 to 10 mm, two grooves 10 are formed in the protuberance 3 of the artificial upper central incisors 1, 15. And as the width of the upper lateral incisor is about 6 to 8 mm, one groove 10 is formed in the protuberance 3 of the artificial upper lateral incisors 17, 19.

The set of artificial teeth of the present invention may also include artificial lower canine teeth opposite to the artificial upper lateral incisors 17, 19, and the labial side face of the artificial lower canine tooth may be provided with a protuberance for forming a sliding surface friction contacting with the frictional surface 5 of the artificial upper lateral incisors 17, 19. Incidentally, the set of artificial teeth of the present invention may also include upper canine and molar teeth. The artificial anterior teeth of the present invention may be connected teeth connected to artificial teeth adjacent in the mesiodistal direction.

In the above embodiment, the labial side surface of the artificial lower anterior teeth 2, 16, 18, 20 is provided with the protuberance 4 for forming the sliding surface 6 friction contacting with the frictional surface 5 formed on the lingual side surface of the artificial upper anterior teeth 1, 15, 17, 19, but the frictional surface 5 of the artificial upper anterior teeth 1, 15, 17, 19 may friction contact with the natural lower anterior teeth, or the vicinity of the cutting edge of the labial side of the artificial lower anterior teeth in a shape simulating natural teeth.

In the present invention, in an ordinary occlusal state, since the lower anterior teeth are positioned at the lingual side of the upper anterior teeth, preferably, the lingual side of the upper anterior teeth should be provided with a protuberance for forming a frictional surface friction contacting with the labial side of the opposite lower anterior teeth, but in the case of counter-occlusion, the lingual side of the lower anterior teeth may be provided with a protuberance for forming a frictional surface friction contacting with the labial side of the opposite upper anterior teeth.

In this regard, when the cutting edge of the opposite teeth is brought into friction contact with the frictional surface, the cutting edge is easily worn out, and hence the portion of the opposite teeth abutting against the frictional surface is preferably a portion slightly away from the cutting edge. Similarly, the frictional surface is preferred to be formed at a position away from the cutting edge.

What is claimed is:

1. An artificial anterior tooth, comprising:
   a cutting edge;
   a cervical portion; and
   a protuberance forming a frictional surface configured to frictionally contact an opposite tooth, the protuberance being configured to extend in a mesiodistal direction, and the frictional surface being dented from the cutting edge to a portion projecting farther than the remainder of the protuberance when viewed from a mesiodistal profile, and having an arch shape imitating a sliding motion of molar teeth as seen from the mesiodistal direction, at a lingual side, wherein
   the protuberance has a groove extending from the cutting edge toward the cervical portion to a portion that does not contact the opposite tooth.

2. The artificial anterior tooth of claim 1, wherein the artificial tooth is an upper anterior tooth.

3. A set of artificial teeth, comprising a plurality of artificial teeth including an artificial anterior tooth as set forth in claim 1.

4. The set of artificial teeth of claim 3 wherein the plurality of artificial teeth includes an artificial anterior tooth opposing the artificial anterior tooth having the frictional surface, and being provided with a protuberance for forming a sliding surface for frictionally contacting the frictional surface.

5. The set of artificial teeth of claim 4, wherein the artificial anterior tooth opposing the artificial anterior tooth having the frictional surface is one of a plurality of artificial anterior teeth opposing the artificial anterior tooth having the frictional surface, and each one of the plurality of artificial anterior teeth opposing the artificial anterior tooth having the frictional surface is provided with a protuberance for forming a sliding surface.

6. A denture, comprising the set of artificial teeth of claim 3 arranged on a denture base.

7. The denture of claim 6, wherein the frictional surface abuts on the labial side of opposite artificial teeth at the intercuspal position.

8. The set of artificial teeth of claim 1, wherein the frictional surface is configured to slide relative to the opposite tooth so as to be capable of grinding food therebetween.

* * * * *